(12) United States Patent
Lai

(10) Patent No.: US 9,289,274 B2
(45) Date of Patent: Mar. 22, 2016

(54) SELF-LIGATING ORTHODONTIC APPLIANCE

(71) Applicant: 3M INNOVATIVE PROPERTIES COMPANY, St. Paul, MN (US)

(72) Inventor: Ming-Lai Lai, Arcadia, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/212,579

(22) Filed: Mar. 14, 2014

(65) Prior Publication Data

US 2014/0272750 A1     Sep. 18, 2014

Related U.S. Application Data

(60) Provisional application No. 61/794,303, filed on Mar. 15, 2013.

(51) Int. Cl.
  *A61C 3/00*       (2006.01)
  *A61C 7/28*       (2006.01)

(52) U.S. Cl.
  CPC ...................... *A61C 7/287* (2013.01)

(58) Field of Classification Search
  CPC ............ A61C 7/28; A61C 7/30; A61C 7/148; A61C 7/287; A61C 7/16; A61C 7/282
  USPC ....................................... 433/8–14
  See application file for complete search history.

(56) References Cited

U.S. PATENT DOCUMENTS

| 5,913,680 | A  | * | 6/1999  | Voudouris  | 433/10 |
|-----------|----|---|---------|------------|--------|
| 6,776,613 | B2 | * | 8/2004  | Orikasa    | 433/11 |
| 6,776,614 | B2 |   | 8/2004  | Wiechmann  |        |
| 6,843,651 | B2 | * | 1/2005  | Orikasa    | 433/13 |
| 7,751,925 | B2 |   | 7/2010  | Rubbert    |        |
| 7,811,087 | B2 |   | 10/2010 | Wiechmann  |        |
| 7,850,451 | B2 |   | 12/2010 | Wiechmann  |        |
| 8,029,276 | B1 | * | 10/2011 | Lokar      | 433/10 |
| 2002/0119414 | A1 | * | 8/2002  | Orikasa  | 433/10 |
| 2003/0039938 | A1 | * | 2/2003  | Orikasa  | 433/11 |
| 2010/0112508 | A1 | * | 5/2010  | Lopes    | 433/10 |
| 2010/0159411 | A1 | * | 6/2010  | Oda      | 433/11 |
| 2010/0285420 | A1 |   | 11/2010 | Oda      |        |
| 2012/0028206 | A1 | * | 2/2012  | Lopes    | 433/10 |
| 2012/0270175 | A1 | * | 10/2012 | Huge et al. | 433/14 |
| 2013/0171579 | A1 | * | 7/2013  | Orikasa  | A61C 7/02 433/10 |

OTHER PUBLICATIONS

Co-pending International Application No. PCT/US13/028785, filed on Mar. 4, 2013, now published as WO2014/018095.
International Search Report for PCT/US2014/028433, prepared by the ISA/US, mailed Aug. 5, 2014.

* cited by examiner

*Primary Examiner* — Cris L Rodriguez
*Assistant Examiner* — Matthew Saunders
(74) *Attorney, Agent, or Firm* — Kevin Weber

(57) ABSTRACT

Provided are orthodontic appliances including a bonding base, a body extending outwardly from the base and an elongated slot extending along the body in a generally mesial-distal direction, and first and second protrusions disposed on the body on opposite sides of the slot. A clip is slidably engaged to the body and movable between open and closed positions. When operating the clip, the first protrusion extends into the clip to retain the clip to the body in an interference fit while the second protrusion extends into the clip when in its closed position. Optionally, the clip comprises at least one deflectable portion aligned along a reference plane extending over the slot, where the deflectable portion resiliently bends out of the reference plane to traverse the second protrusion as the clip moves between open and closed positions.

19 Claims, 8 Drawing Sheets

SELF-LIGATING ORTHODONTIC APPLIANCE

FIELD OF THE INVENTION

This invention relates to bondable appliances used in orthodontic treatment and methods related thereof. More particularly, the invention relates to bondable appliances that are self-ligating and methods related thereof.

BACKGROUND

Orthodontics is a specialized field of dentistry concerned with the therapeutic movement of malpositioned teeth into proper positions. Orthodontic treatment can provide many benefits to a patient, including improved bite function and speech, enhanced facial aesthetics, and easier maintenance of dental hygiene. To move teeth, the orthodontic practitioner generally prescribes the use of corrective appliances that mechanically engage to the patient's teeth and apply gentle continuous forces that gradually move the teeth into orthodontically correct positions. Treatment often lasts between two and three years, depending on the complexity of the case.

A common mode of treatment uses tiny slotted appliances called orthodontic brackets, which are adhesively attached to the surfaces of the teeth. A resilient arch-shaped wire ("archwire") is generally tied, or "ligated," into the slot of each bracket. The ends of the archwire are generally captured in tube-shaped appliances called molar tubes, which are affixed to the patient's molar teeth. While the archwire is initially distorted when ligated to the brackets, it gradually returns toward its original shape, functioning as a track that guides movement of teeth toward desired positions. The brackets, tubes, and archwire are collectively known as "braces."

Traditional brackets are ligated to the archwire with the help of one or more pairs of opposing tiewings, which are cleat-like projections on the bracket body. The archwire is placed in the archwire slot and generally a tiny elastomeric "O"-ring ligature, or alternatively a metal ligature wire, is fastened over the archwire and beneath the undercut portions of tiewings located on opposite sides of the archwire slot. In this manner, the ligature secures the archwire in the archwire slot of each bracket and obtains a mechanical coupling between these bodies.

The use of ligatures, however, can present numerous drawbacks. When initially installed, for example, elastomeric ligatures tend to secure the archwire very tightly, resulting in relatively high resistance to sliding. In certain stages of treatment, for example when teeth are being leveled and aligned, this can undesirably slow teeth movement. These ligatures also have a tendency to lose elasticity, causing the sliding mechanics of the archwire to change over time. Moreover, the process of stretching each "O"-ring over the archwire and under the tiewings of each bracket can be cumbersome and time-consuming for the orthodontic practitioner. Finally, ligatures can trap food or plaque in areas beneath the bracket tiewings, making cleaning areas around the brackets more difficult. The use of ligature wire results in many of the same problems as elastomeric ligatures above.

Self-ligating brackets can alleviate many of the above problems. These appliances typically use a permanently installed movable component, such as a clip, spring member, door, shutter, bail, or other ligation mechanism. This mechanism encloses the archwire in the archwire slot, obviating a separate ligature. In many cases, self-ligating brackets still include tiewings on the bracket body in the event that the practitioner desires to further secure the archwire in the slot using a separate ligature. In some cases, ligatures may be so used when the practitioner desires to fully seat the archwire into the slot or increase friction between archwire and bracket to further a particular treatment goal.

The ligation mechanism of self-ligating brackets offers many potential advantages. For example, these appliances can decrease friction between the archwire and the bracket compared with brackets ligated with elastomeric ligatures, potentially providing faster movement of teeth in early stages of treatment. Depending on the mechanism, these appliances can also simplify the installation and removal of an archwire, thereby reducing chair time for the treating professional. Finally, self-ligating brackets can also avoid the hygiene issues of conventional brackets above.

Some self-ligating brackets provide "active ligation" by imparting forces to seat a ligated archwire into its archwire slot, enabling the prescription of the appliance to be fully expressed during treatment. The intended benefit of such a configuration is that, in general terms, the range of engagement (e.g., labial-lingual engagement) between the bracket and wire is increased, thus resulting in improved control and alignment of teeth in treatment. By contrast, "passive" self-ligating brackets have a slot depth sufficiently large such that the ligating door does not exert a continuous force seating the archwire into the slot. Still other brackets are engineered to be either active or passive, depending on the size and configuration of the archwire.

SUMMARY

In planning an orthodontic treatment, a practitioner often desires to exercise precise control over degree of coupling between bracket and archwire. Self-ligating brackets that use a rigid door-type mechanism are often passive in nature, particularly when the door has a fixed position relative to the slot. Other self-ligating brackets use a springy and resilient "U"-shaped clip to provide for active ligation. These mechanisms, however, have their own disadvantages. For example, these appliances generally require a higher labial-lingual profile to accommodate both "legs" of the U-shaped clip. Additionally, repeatedly sliding the mechanism open and closed can impart a moment to one leg of the clip, which can permanently deform the clip over time. Consequently, there is need for a self-ligating appliance capable of providing active ligation without the associated disadvantages of existing active ligation mechanisms.

In one aspect, an orthodontic appliance is provided. The orthodontic appliance comprises: a base having a bonding surface for attachment to a tooth; a body extending outwardly from the base and an elongated slot thereon extending along a generally mesial-distal direction; first and second protrusions disposed on the body with the slot extending therebetween; and a clip slidably engaged to the body and movable between open and closed positions to admit or deny access to the slot, the first protrusion extending into the clip to retain the clip to the body in an interference fit and the second protrusion extending into the clip in its closed position selectively, wherein the clip comprises at least one deflectable portion aligned along a reference plane extending over the slot and wherein the at least one deflectable portion resiliently bends out of the reference plane to traverse the second protrusion as the clip moves between open and closed positions.

In another aspect, an orthodontic appliance is provided, comprising: a base having a bonding surface for attachment to a tooth; a body extending outwardly from the base and having an elongated slot thereon extending along a generally mesial-distal direction; a resilient clip comprising mesial and distal struts slidably engaged to the body to enable movement of the clip between open and closed positions for admitting or denying access to the slot, and an open region located between the mesial and distal struts; and first and second protrusions disposed on the body with the slot extending therebetween, wherein both protrusions occupy the open region when the clip is closed and only the first protrusion occupies the open region when the clip is open.

In yet another aspect, a method of using an orthodontic appliance is provided, comprising: providing the appliance comprising a base, a body extending outwardly from the base, an elongated slot extending along a generally mesial-distal direction disposed on the base, and first and second protrusions located on the body on opposite sides of the slot; providing a clip having an open region slidably engaged to the body, wherein the first protrusion occupies the open region to retain the clip in an interference fit and the second protrusion resides outside of the open region; sliding the clip from an open position toward a closed position whereby a first deflectable portion of the clip urges against the second protrusion; and resiliently bending the first deflectable portion to enable the clip to traverse the second protrusion and position both the first and second protrusions within the open region to retain the clip in the closed position.

DEFINITIONS

Figure 1:
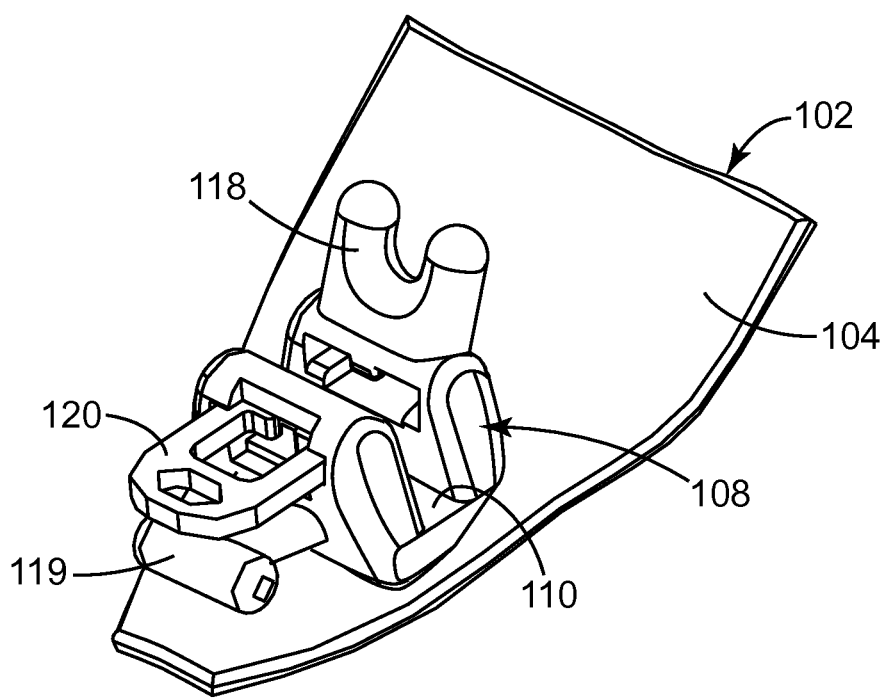
FIG. 1 is a perspective view of an orthodontic appliance according to one embodiment of the present disclosure in an open configuration, looking toward its lingual, mesial, and gingival surfaces.

As used herein:
"Mesial" means in a direction toward the center of the patient's curved dental arch.
"Distal" means in a direction away from the center of the patient's curved dental arch.
"Occlusal" means in a direction toward the outer tips of the patient's teeth.
"Gingival" means in a direction toward the patient's gums or gingiva.
"Labial" means in a direction toward the patient's lips or cheeks.
"Lingual" means in a direction toward the patient's tongue.

DETAILED DESCRIPTION

The following sections further examine particular embodiments of the invention directed to self-ligating orthodontic appliances and related methods of ligation. The illustrated embodiments in this disclosure are exemplary and should not be construed to unduly limit the invention. One of ordinary skill can adapt the disclosed appliances, kits, and methods for attachment to either the labial or lingual surfaces of teeth, to different teeth within the same dental arch, and to teeth of either the upper or lower dental arches. While the appliances described herein have a configuration for occlusal insertion of archwires, a skilled artisan can re-orient components of these appliances to provide for labial or lingual insertion of archwire.

The appliances and methods described herein may also either be customized or non-customized to the individual patient undergoing treatment. Exemplary methods of digitally rendering and fabricating customized appliances are described in U.S. Pat. No. 6,776,614 (Wiechmann, et al.), U.S. Pat. No. 7,811,087 (Wiechmann, et al.), U.S. Pat. No. 7,751,925 (Rubbert, et al.), and U.S. Pat. No. 7,850,451 (Wiechmann, et al.).

Additionally, material and dimensional specifications and intended methods of use could vary from those disclosed herein without departing from the scope of the claimed invention.

A lingual orthodontic appliance according to one embodiment, designated by the numeral 100, is shown in various views in FIGS. 1-5. As illustrated, the appliance 100 includes a base 102 having an inner surface 104 and an outer, bonding surface 106 (shown in the distal side view of FIG. 5). In a preferred embodiment, the outer surface 106 has an overall shape that facilitates adhesive bonding to the tongue-facing surfaces of a patient's tooth. The outer surface 106 can optionally have holes, grooves, recesses, undercuts, partially embedded particles, mesh, a chemical bond enhancement material, a micro-etched surface, or any other material, structure, or combination thereof, to improve mechanical retention between the appliance 100 and the tooth.

Figure 5:
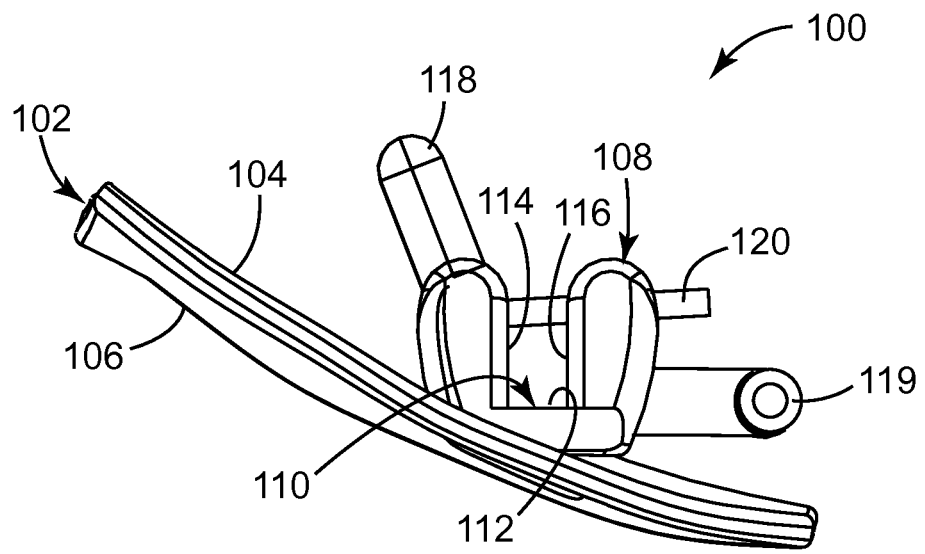
FIG. 5 is a distal side view of the appliance of FIGS. 1-4, looking toward its distal-facing surfaces.

Extending outwardly from the inner surface 104 is a body 108. In some embodiments, the body 108 and base 102 can be welded, soldered, or adhesively coupled to each other. Alternatively, the body 108 and base 102 can be integrally formed, for example, by investment casting or any of a number of known rapid prototyping methods. An elongated archwire slot 110 extends across the occlusal-facing surface along a generally mesial-distal direction, and has an orientation and location enabling a suitably sized archwire to be received in the body 108 during orthodontic treatment. As shown in FIG. 5, the slot 110 has a generally rectilinear configuration that includes a planar bottom wall 112 and planar labial and lingual side walls 114, 116, each perpendicular, or at least substantially perpendicular, to the bottom wall 112.

Optional tiewings 118 and an optional hook 119 are integrally formed with the body 108 to provide for manual ligation of an archwire in the slot 110 and further to provide for attachment of orthodontic auxiliaries, if desired.

Optionally and as shown, the body 108 has an orientation relative to the base 102 where the bottom wall 112 is oriented at an acute angle with respect to the inner and outer surfaces 104, 106 of the base 102. For appliances bonded to the labial surfaces of teeth, which are generally more vertically aligned, it may be preferred for the bottom wall 112 to be generally parallel with the inner and outer surfaces 104, 106 to assist with archwire insertion into the slot 110.

In exemplary embodiments, either the base 102, body 108, or both are integrally manufactured from a metal having suitable strength and modulus, such as a stainless steel, titanium or gold alloy. In some embodiments, the appliance 100 is a labial appliance that is visible during treatment; if so, the base 102 and/or body 108 can be made from a translucent ceramic material. Particularly preferred ceramic materials include the fine-grain polycrystalline alumina materials described in issued U.S. Pat. No. 6,648,638 (Castro, et al.). These ceramic materials are known for their high strength and also provide superior aesthetics compared with metallic materials because they transmit light and can visually blend in with the color of the underlying tooth surface. Because of their aesthetic properties, ceramics are naturally advantageous for labially-bonded appliances, but can also be broadly useful for lingual appliances when patient have nickel-allergies or other oral sensitivities to metal.

Figure 2:
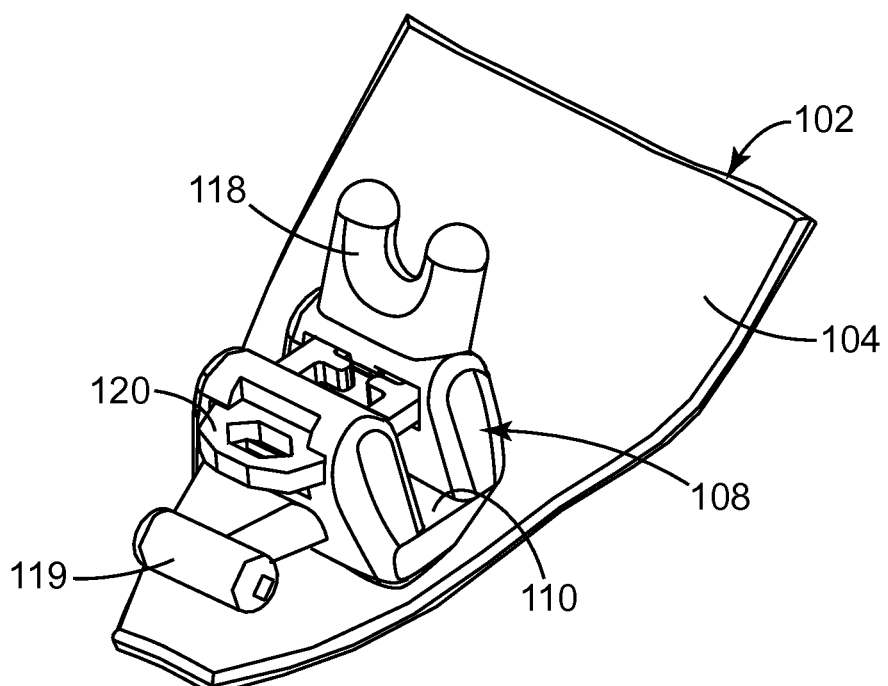
FIG. 2 is a perspective view of the appliance of FIG. 1 in a closed configuration, looking toward its lingual, mesial, and gingival surfaces.
Figure 3:
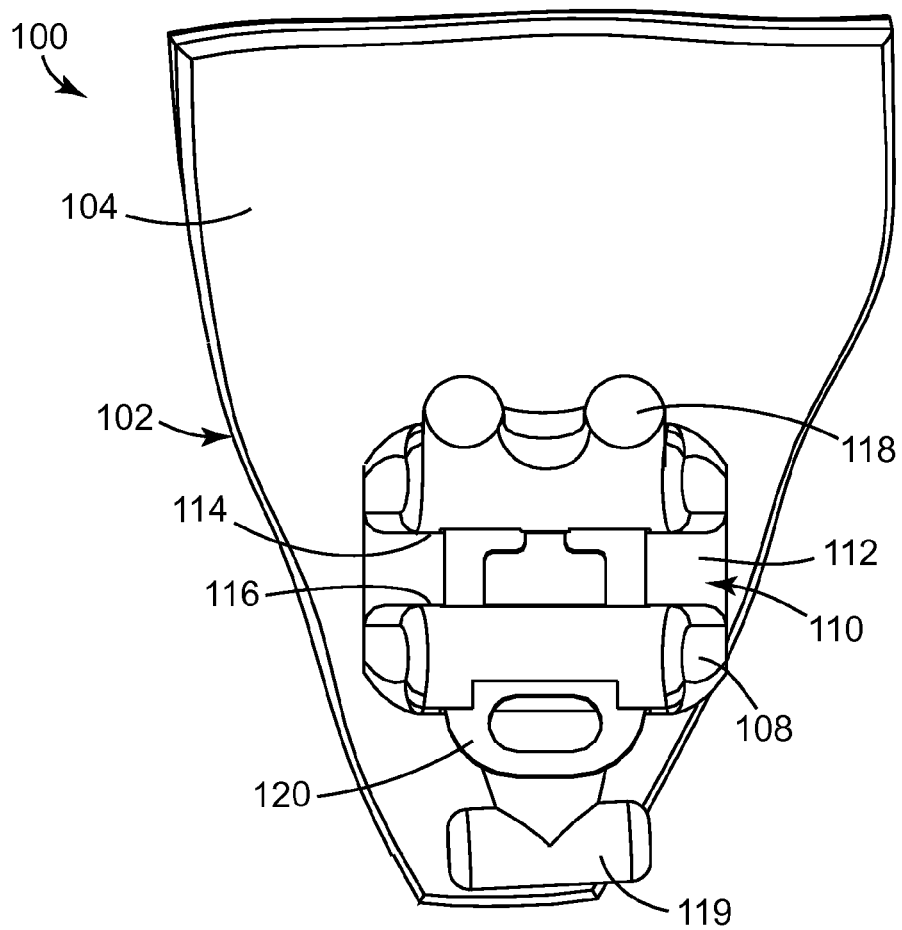
FIG. 3 is an occlusal view of the appliance of FIGS. 1-2, looking toward its occlusal-facing surfaces.
Figure 4:
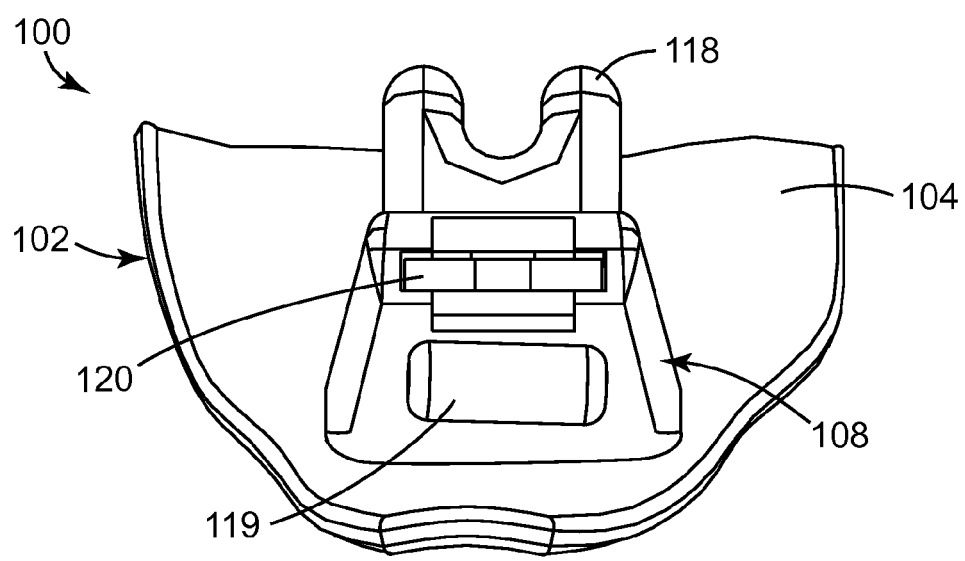
FIG. 4 is a lingual view of the appliance of FIGS. 1-3, looking toward its lingual-facing surfaces.

As further shown in FIGS. 1-5, a resilient and generally planar clip 120 is slidably received in the occlusal side of the body 108 and is movable between open and closed positions to either admit or deny access of the archwire to the slot 110 from a particular direction. FIGS. 1-2 show in particular the clip 120 in open and closed positions, respectively.

Figure 6:
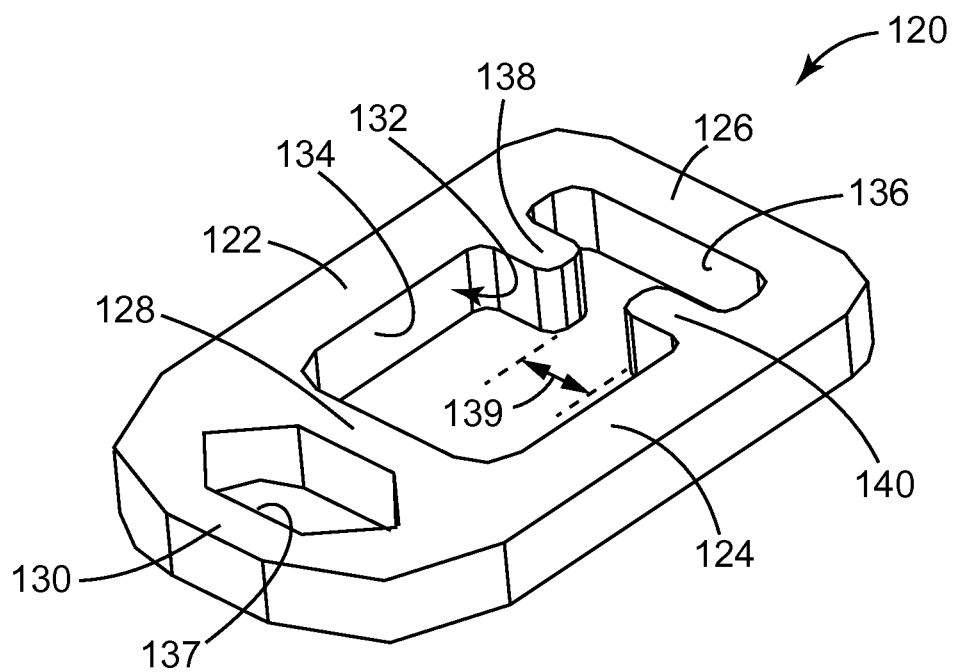
FIG. 6 is a perspective view of a sliding component of the appliance of FIGS. 1-5.

Further aspects of the clip 120 are shown in more detail in FIG. 6. As shown, the clip 120 has a generally planar, rectangular configuration that includes mesial and distal struts 122, 124, a deflectable front strut 126, and first and second back struts 128, 130. The mesial and distal struts 122, 124 extend along a generally labial-lingual direction that corresponds to the path of travel of the clip 120 when assembled to the body 108. The front strut 126 and back struts 128, 130 extend perpendicular to the mesial and distal struts 122, 124 and connect the mesial and distal struts 122, 124 to each other, with the front strut 126 positioned at the leading edge of the clip 120 and the back struts 128, 130 positioned toward the trailing edge of the clip 120.

The mesial and distal struts 122, 124, along with front strut 126 and first back strut 128, each extend along and define an open region 132. As shown here, the open region 132 is fully enclosed by the clip 120, but this need not be the case. One or more discontinuities could be present in one or more of the struts 122, 124, 126, 128 without compromising the overall functionality of the clip 120.

As further shown in FIG. 6, the open region 132 is subdivided into a first open region 134 and a second open region 136 adjacent the first open region 134 by a pair of deflectable tabs 138, 140. The tabs 138, 140 protrude inwardly toward each other from the mesial and distal struts 122, 124, and are spaced apart from each other by a gap 139 at their point of closest approach. In sum, the back strut 128, the mesial and distal struts 122, 124, and the tabs 138, 140 collectively define the first open region 134, while the front strut 126, the mesial and distal struts 122, 124, and the tabs 138, 140 collectively define the second open region 136.

In the illustrated embodiment, the first and second open regions 134, 136 are characterized by a certain mesial-distal width. With the first and second open regions 134, 136 being approximately rectangular in shape, the mesial-distal width of these regions 134, 136 is generally consistent along the length of the mesial and distal struts 122, 124. In some embodiments, the gap 139 has a magnitude of at least 0 percent, at least 5 percent, at least 15 percent, at least 45 percent, or at least 80 percent of the mesial-distal width of the first and second open regions 134, 136. In some embodiments, the gap 139 has a magnitude of at most 100 percent, at most 80 percent, at most 60 percent, at most 40 percent, or at most 20 percent of the mesial-distal width of the first and second open regions 134, 136.

FIG. 6 also shows a third open region 137 enclosed by the mesial and distal struts 122, 124 and the pair of back struts 128, 130. The third open region 137 is adjacent to the first open region 134, on its lingual side, and provides a purchase point for a pointed hand instrument used to operate the clip 120.

Preferably the clip 120 is made from one or more resilient materials having a high elastic strain limit, such as a shape memory material based on an alloy of nickel and titanium, although other materials such as stainless steel, beta titanium, cobalt alloys (e.g., from Elgiloy Specialty Metals, Elgin, Ill.), or even certain plastic materials may be used so long as they do not fatigue or fracture during the course of repeated opening and closing of the clip 120.

Figure 7:
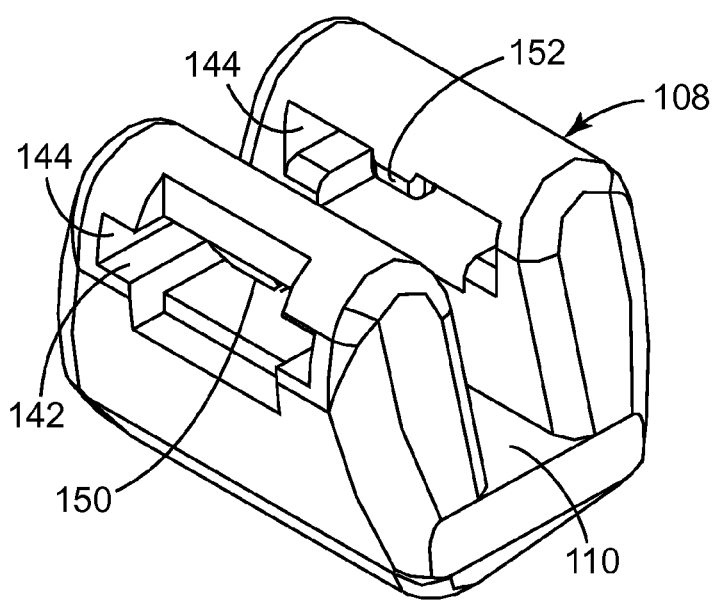
FIG. 7 is a perspective view of a fixed component of the appliance of FIGS. 1-5, looking toward its lingual, mesial, and gingival surfaces.
Figure 8:
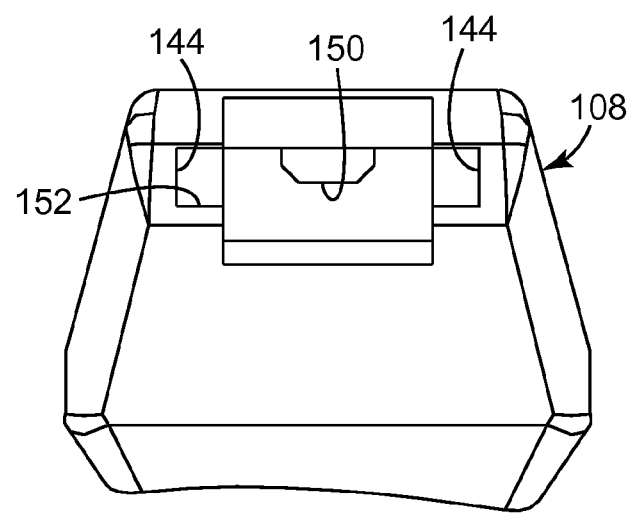
FIG. 8 is a lingual view of the fixed component of FIG. 7, looking toward its lingual-facing surfaces.
Figure 9:
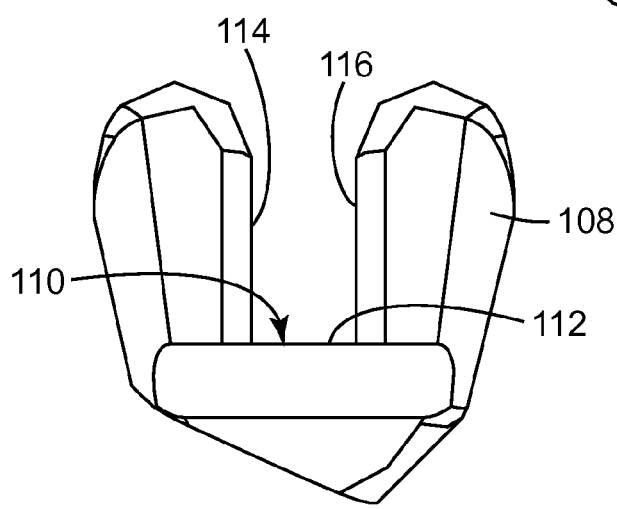
FIG. 9 is a distal side view of the fixed component of FIGS. 7-8, looking toward its distal-facing surfaces.

The interaction between the clip 120 and the body 108 can be further clarified by reference to FIGS. 7-9, which show relevant portions of the body 108 that engage with the clip 120. A channel 142 extends through at least a portion of the body 108. As illustrated in FIGS. 7-8, the channel 142 has undercuts 144 for receiving the mesial and distal struts 122, 124 of the clip 120 (omitted from FIGS. 7-9 for clarity). FIG. 7 shows that the undercuts 144 are disposed on opposite sides of the archwire slot 110, thus preventing the clip 120 from becoming disengaged from the body 108 even when outward pressure is applied by an archwire received in the slot 110. While not essential, the body 108 can also extend over and across the channel 142 on both sides of the archwire slot 110 as shown in FIG. 7.

Referring again to FIGS. 7-8, a first protrusion 150 and a second protrusion 152 project from the body 108 in a direction toward the base 102 into the channel 142. The protrusions 150, 152 are disposed along the channel 142 on opposite sides of the archwire slot 110. As will be further explained in the sections below, the protrusions 150, 152 mechanically interact with the front and back struts 126, 128 and the tabs 138, 140 as the clip 120 slides through the channel 142. This interaction facilitates operation of the appliance 100 by defining stable open and closed clip positions.

Referring back to FIG. 6, the front strut 126 and tabs 138, 140 each represent deflectable portions of the clip 120 capable of resiliently bending out of the plane of the clip 120 as the clip 120 is slidably moved between opened and closed positions on the body 108. In such implementations, a deflecting region of the clip includes the two deflectable portions (i.e., the front strut 126 and tabs 138,140). The clip 120 need not include all of the features depicted in FIG. 6. For example, the tabs 138, 140, back strut 130, and third open region 137 could be omitted from a simplified variant of the clip 120. In this variant, the front strut 126 could function alone as the deflectable portion of the clip 120 (i.e., the deflecting region includes only the front strut 126).

Figure 10:
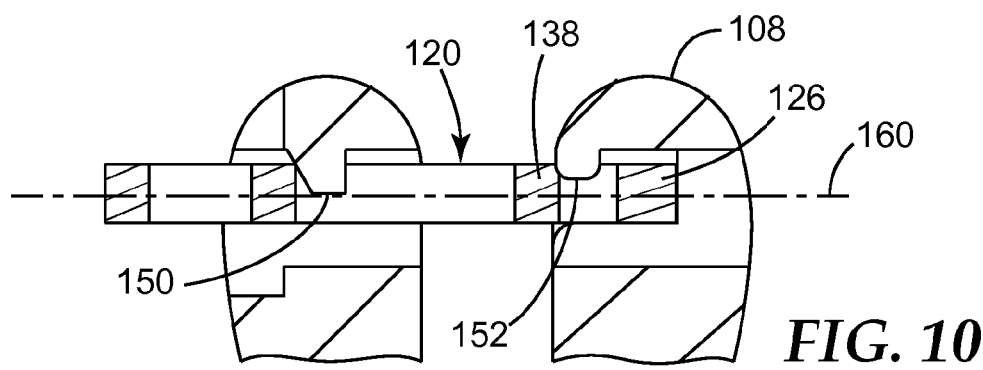
FIG. 10 is a fragmentary cross-sectional side view of the appliance of FIGS. 1-5 in a closed configuration, showing its mesial-facing cross-sectional surfaces.

The operation of the clip 120 as it slides relative to the body 108 is shown on an enlarged scale in the cross-sectional illustrations of FIGS. 10-13. FIG. 10 shows the clip 120 in its stable closed position, in which the second protrusion 152 extends into and occupies the second open region 136 (between the front strut 126 and the tabs 138, 140. By virtue of the second protrusion 152 having an overall mesial-distal width that is greater than the gap 139 between the tabs 138, 140, the second protrusion 152 is held captive within the second open region 136 during the normal course of treatment.

In the configuration shown in FIG. 10, both of the protrusions 150, 152 occupy the collective open region 132. More specifically, the first protrusion 150 occupies the first open region 134 and the second protrusion 152 occupies the second open region 136. In certain advantageous implementations, the first and second protrusions 150, 152 can be positioned relative to each other so as to simultaneously engage the front and back struts 126, 128, respectively, thereby restricting inadvertent sliding movement of the clip 120 while in its closed position shown.

Figure 11:
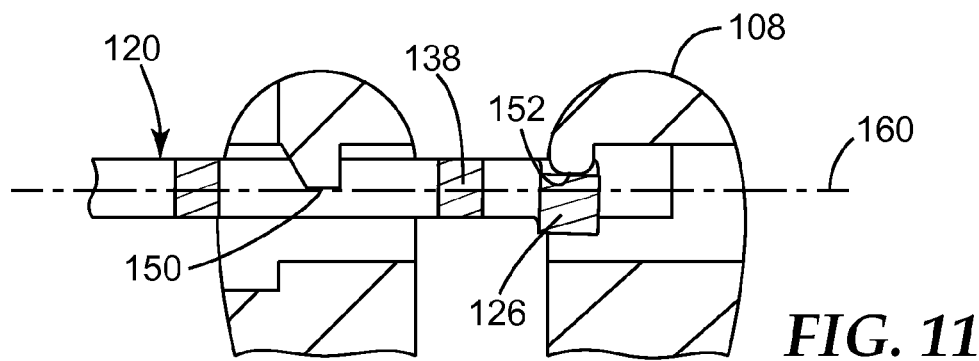
FIGS. 11 and 12 are fragmentary, cross-sectional side views of the appliance of FIGS. 1-5 in partially open configurations, showing their mesial-facing cross-sectional surfaces.

To open the clip 120, a practitioner can insert the tip of an explorer or other suitable hand instrument into the third open region 137, and apply a lingual sliding force to the clip 120. FIG. 11 shows the clip 120 in a different position after the application of a lingual sliding force as it is urged from its closed position toward its open position. In this figure, essentially the entire clip 120, including the front strut 126, resides along a reference plane 160 that extends over the entrance of the archwire slot 110. When the clip 120 slides to the position shown in the FIG. 11, resistance to further sliding has increased as a result of the protrusion 152 coming into contact with the front strut 126. When urged against the protrusion 152 with sufficient force, the front strut 126 of the clip 120 can resiliently deflect out of the reference plane 160 as shown, and traverse the protrusion 152 to reach a partially opened clip configuration as shown in FIG. 12.

The reference plane 160 is generally coplanar with the sliding direction of the clip 120. Optionally and as shown, the reference plane 160 extends over the occlusal-facing entrance of the archwire slot 110 and is parallel the bottom wall 112. Alternatively, the reference plane 160 may extend at some acute angle relative to the bottom wall 112. Such a configuration may be desirable where, for example, angling the clip 120 relative to the body 108 enables an overall lower profile appliance 100 or aligns the clip 120 in a direction that avoids potential irritation to cheeks or lips of the patient during treatment. In other implementations, the reference plane 160 can be defined by the channel 142 and/or one or more of the protrusions 150, 152.

Figure 12:
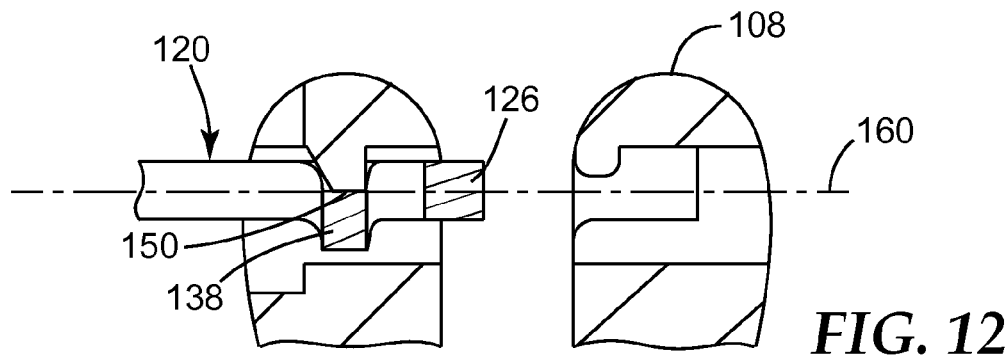
Figure 13:
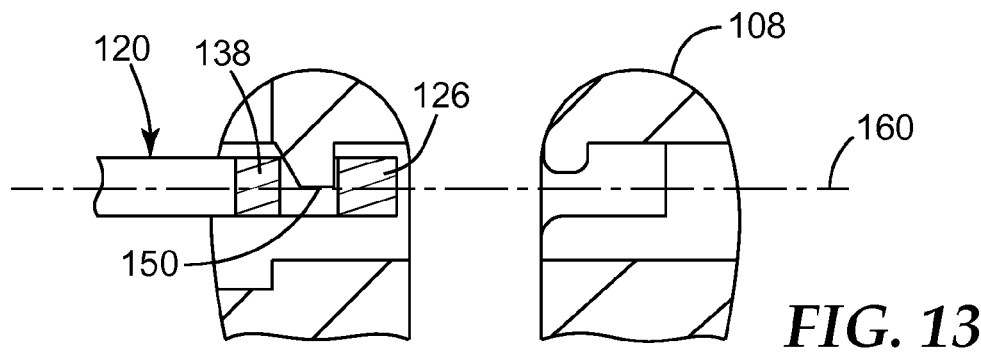
FIG. 13 is a fragmentary, perspective cross-sectional view of the appliance of FIGS. 1-5 in a fully open configuration, showing its mesial-facing cross-sectional surfaces.

In the clip configuration shown in FIG. 12, the second protrusion 152 is located outside of the clip 120 without occupying either of the first or second open regions 134, 136. The first protrusion 150, however, remains in the first open region 134 and comes into contact with the tabs 138, 140. Again, under sufficient force, the tabs 138, 140 can resiliently bend, or deflect, out of the reference plane 160 to traverse the first protrusion 150 and allow the clip 120 to assume the fully opened position shown in FIG. 13. Optionally and as shown, the first protrusion 150 simultaneously engages the front strut 126 and the tabs 138, 140 to hold open the clip 120 and restrict further sliding movement. Therefore, the first and second protrusions 150, 152 occupy respective first and second open regions 134, 136 when the clip 120 is closed, while the first protrusion 150 occupies the second open region 136 and the second protrusion 152 occupies neither of the first and second open regions 134, 136 when the clip 120 is open.

From this open position, the clip 120 can be subsequently closed by using a hand instrument to apply a labial force at the third open region 137 of the clip 120. If so desired, a practitioner could also direct forces against one of the other open regions 134, 136 (if accessible) or front or back struts 126, 128, to slidably close the clip 120. The process of closing the clip 120 essentially tracks the above steps in reverse.

Various engineering considerations can inform the shape and size of the first and second protrusions 150, 152 and the tabs 138, 140. For example, the first protrusion 150 can be made larger than the second protrusion 152 such that the front strut 126 of the clip 120 is capable of traversing the latter under usual clip opening forces but will not traverse the former under the same forces, lest the clip 120 become completely dislodged from the body 108. Opening and closing forces of the clip 120 are typically at least 0.4 N (0.1 lbf), in some embodiments at least 0.9 N (0.2 lbf), and in yet other embodiments at least 2 N (0.4 lbf). Opening and closing forces of the clip 120 are typically no greater than 49 N (11 lbf), in some embodiments no greater than 18 N (4.0 lbf), and in yet other embodiments no greater than 13 N (3.0 lbf).

The geometry of the protrusions 150, 152 can also be used to adjust the forces required to open and close the clip 120. For example, the forces required to open and close the clip 120 could be decreased by using protrusions 150, 152 having a generally trapezoidal profile with sloping side walls (as viewed from the mesial or distal direction). For one or both protrusions 150, 152, one or both side walls could be characterized by a side wall angle of less than about 60 degrees, less than about 45 degrees, or less than about 30 degrees. Similarly, one or both protrusions 150, 152 could have a side wall angle greater than about 45 degrees, greater than about 60 degrees, or greater than about 75 degrees. Further aspects of trapezoidal protrusions are described in co-pending International Application No. PCT/US13/28785 (Vick et al.), filed on Mar. 4, 2013.

If desired, asymmetric opening and closing forces can be realized by using a trapezoidal protrusion with substantially different side wall angles. For example, one side of the protrusion 150, 152 could have a side wall angle of 40 degrees, while the opposing side of the protrusion 150, 152 could have a side wall angle of 60 degrees. Such a configuration could be used to decrease forces required to close the clip 120 while maintaining higher threshold levels of force to open the clip 120 to avoid accidental wire disengagement during treatment.

The shapes of the tabs 138, 140 can also be modified to adjust the level of force required to snap the clip 120 between open and closed positions. For example, the tabs 138, 140 could be made narrower, or the contours of the tabs 138, 140 further rounded, to decrease the force required to open the clip 120.

As yet another alternative, the tabs 138, 140 could be substituted by a different deflectable component of the clip 120. For example, the clip 120 could instead include an intermediate strut that interconnects the mesial and distal struts 122, 124 and has sufficient flexibility to deflect out of the reference plane 160 and traverse the first protrusion 150 as the clip 120 is opened.

Figure 14:
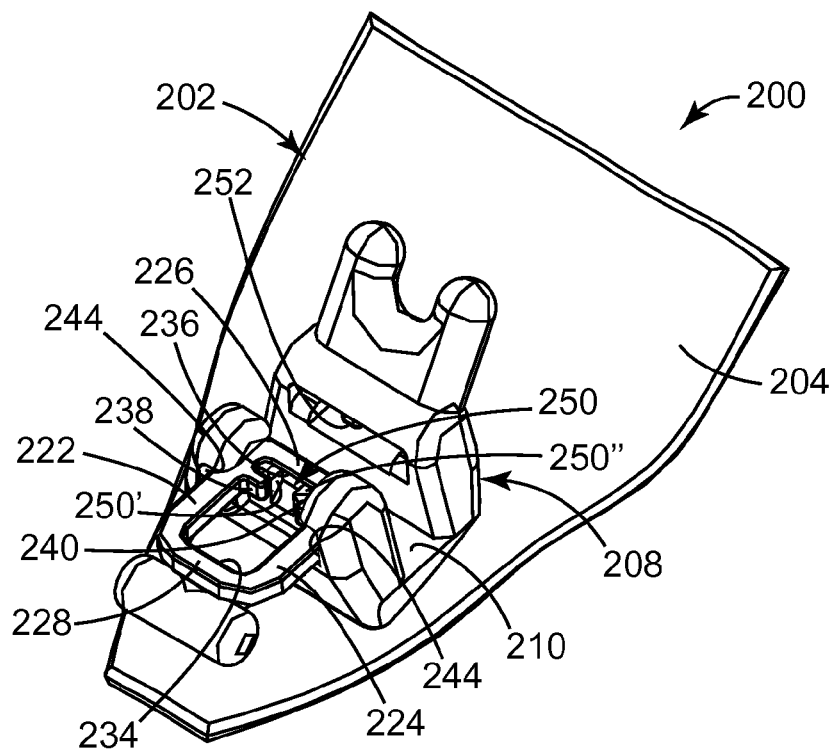
FIG. 14 is a perspective view of an orthodontic appliance according to another embodiment of the present disclosure in an open configuration, looking toward its lingual, mesial, and gingival surfaces.
Figure 15:
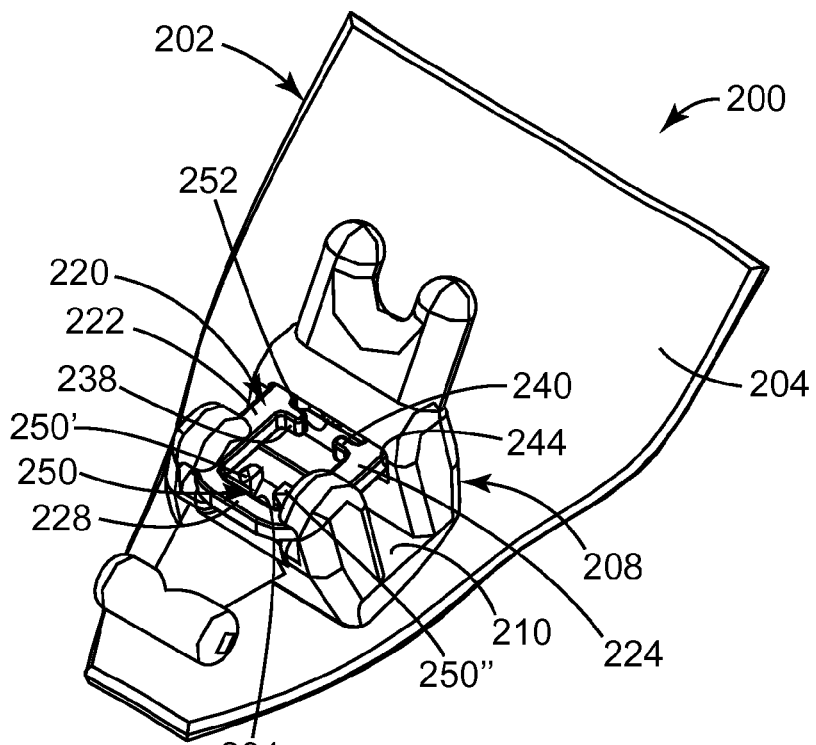
FIG. 15 is a perspective view of the orthodontic appliance of FIG. 14 in a closed configuration, looking toward its lingual, mesial, and gingival surfaces.
Figure 16:
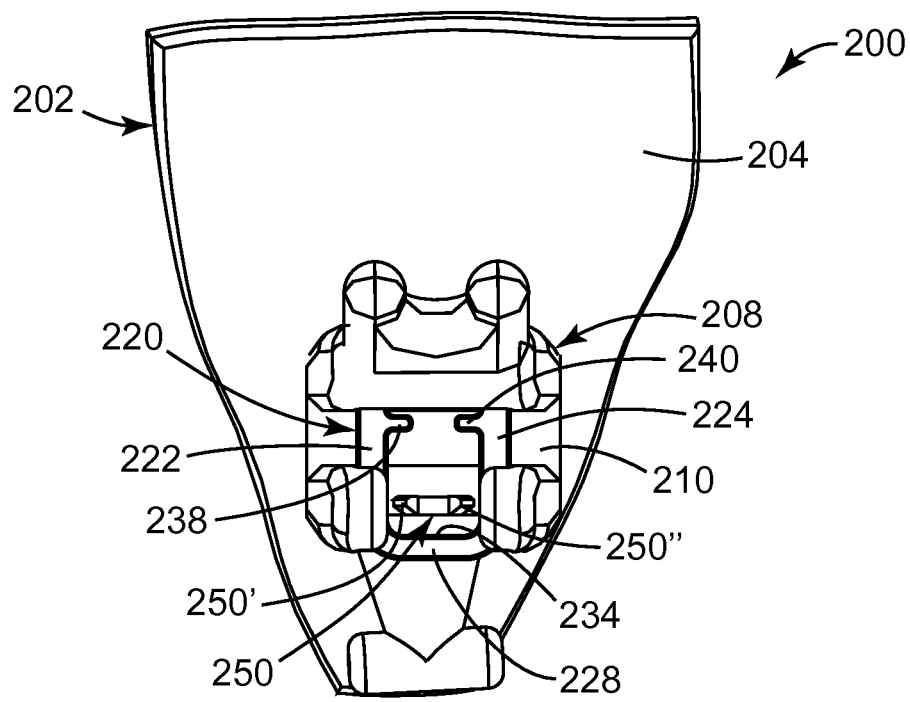
FIG. 16 is an occlusal view of the appliance of FIGS. 14-15, looking toward its occlusal-facing surfaces.

Another exemplary embodiment is represented by the orthodontic appliance 200 in FIGS. 14-16. Like appliance 100, the appliance 200 has a base 202 having an inner surface 204, a body 208 extending from the inner surface 204, and a mesial-distal extending archwire slot 210, with a clip 220 capable of reversibly sliding over the slot 210. The clip 200, however, bears several technical and functional differences from the appliance 100.

First, the clip 220 does not have a pair of back struts that define a third open region. Instead, the clip 220 has only a deflectable front strut 226, a back strut 228, and pair of opposing tabs 238, 240 located between its mesial and distal struts 222, 224. As before, the clip 220 has a first open region 234 and a second open region 236 set apart from each other by the opposing tabs 238, 240. In this embodiment, however, the sliding engagement of the clip 220 and the body 208 is achieved using an open-faced channel having undercuts 244. As FIG. 15 illustrates, the body 208 does not fully extend over the occlusal face of the clip 220 along a mesial-distal direction when the clip 220 is opened.

Unlike the first open region 134 in the prior embodiment, the first open region 234 is fully accessible to the pointed tip of a hand instrument along the full range of sliding motion of the clip 220. Preferably, the first open region 234 has a size sufficient to accommodate the pointed tip of a common hand instrument such as an explorer or scalar to operate the clip 220. Advantageously, this configuration allows the clip 220 to be made considerably shorter, enabling the back strut 228 of the clip 220 to be essentially flush with the lingual side of the body 208 when the clip 220 is closed (as shown in FIG. 14). With the clip 220 fully withdrawn into the body 208 during treatment, it is less likely to cause patient irritation.

Second, the appliance 200 includes first and second protrusions 250, 252 that extend in opposite directions. The first protrusion 250, which is bifurcated into a pair of subprotrusions 250', 250", extends from the body 208 in a generally occlusal direction away from the base 202 into either the first or second open region 234, 236 of the clip 220. The second protrusion 252, which extends from the body 208 in a direction toward the base 202 in a generally gingival direction, operates similarly to the second protrusion 152 in retaining the clip 220 in its closed position as shown in FIG. 14. Here, the subprotrusions 250', 250" collectively have a mesial-distal width equivalent to the first protrusion 250. As an alternative, the second protrusion 252 can also extend in a direction away from the base 204.

Further aspects and advantages of the appliance 200 are analogous to those already described with respect to the appliance 100 and shall not be repeated.

In the above embodiments, the clips 120, 220 are generally planar and generally aligned along respective reference planes 160, 260. As an alternative, the clip 120, 220 could have a slight curvature in which the path of sliding is defined along a curved surface. In these embodiments, the reference planes 160, 260 could be represented as planes that are approximately tangent to the curved surface. Using a clip 120, 220 that curves toward its respective base 102, 202 could be beneficial in reducing the overall profile of the appliance 100, 200 and improve patient comfort, particularly when the clip 120, 220 protrudes beyond the body 108, 208 when closed.

Figure 17:
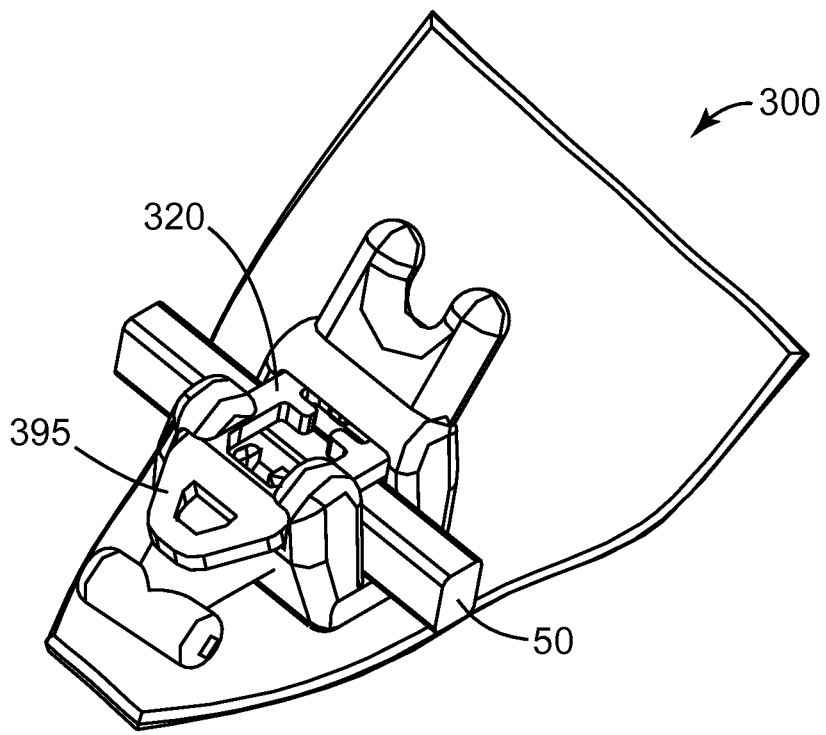
FIG. 17 is a perspective view of an orthodontic appliance according to still another embodiment of the present disclosure in an open configuration, looking toward its lingual, mesial, and gingival surfaces.

FIG. 17 shows an appliance 300 according to still another embodiment that exemplifies another approach to decreasing overall appliance profile. In the figure, the appliance 300 includes a clip 320, shown retaining an archwire 50 in the appliance 300. The clip 320 is similar to the clip 220 in most respects except the lingual side of the clip 320 includes an added flap 395 bent at an angle relative to the rest of the clip 320. The flap 395 is oriented at an angle toward the base of the appliance 300 and provides a purchase point for engaging the clip 320 while helping preserve an overall low profile.

Preferably, the clips 120, 220, 320 are not only resilient but capable of flexing significantly in response to forces typically imposed by the archwire during the course of orthodontic treatment. The use of a flexible clip enables configurations where the archwire imparts a force to the appliance over a wide range of motion, resulting in "active ligation."

Figure 18:
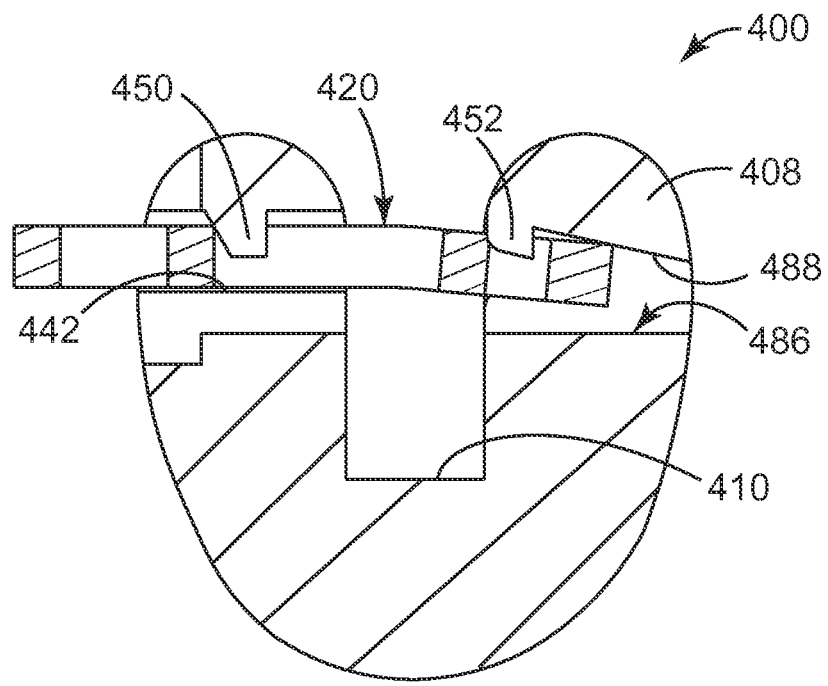
FIG. 18 is a perspective view of a fixed component of an appliance according to yet another embodiment of the present disclosure.
Figure 19:
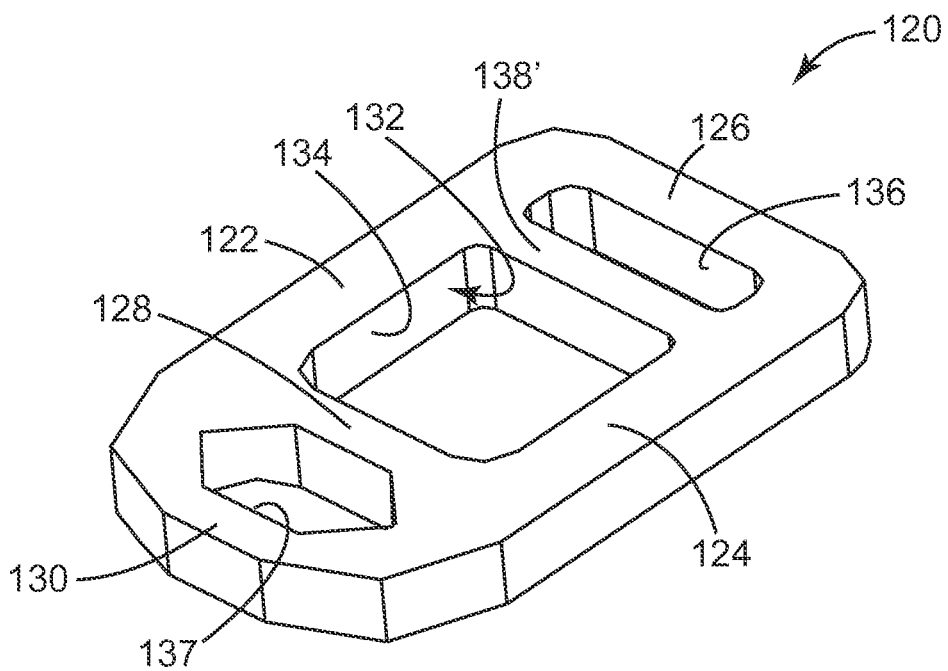
FIG. 19 is a perspective view of another embodiment of a sliding component for use in the appliances of the present disclosure.

FIG. 18 shows relevant portions of an orthodontic appliance 400 according to yet another embodiment that provides active ligation. As shown, the appliance includes a body 408 having protrusions 450, 452 located on opposite sides of an archwire slot 410. The protrusions 405, 452 are shown releasably locking the clip 420 in its closed position, as understood from previous embodiments. The clip 420, which slides along a channel 442, is partially received in a cavity 486 having an entrance facing a generally lingual direction. The cavity 486 includes an angled wall 488 that slopes in a generally gingival direction toward the base of the appliance 400 (not visible). As a result of contacting the angled wall 488, the clip 420 is deflected toward the gingival direction, decreasing the space between the clip 420 and the bottom wall of the slot 410.

Optionally, the angled wall 488 can adopt any suitable orientation with respect to the channel 442 to provide a desired degree of activation. For example, providing the angled wall 488 with a steeper slope will result in greater deflection of the clip 420 and further reduce the space within the slot 410. As a result of this modification, the passive range of motion of a ligated archwire within the slot 410 would decrease. The range of active ligation, by contrast, would increase since the clip 420 is capable of deflecting toward the occlusal direction away from the base of the appliance 400 in response to occlusal forces exerted by the archwire. In some embodiments, the angled wall 488 can have a spacing and orientation that enables "active ligation" whenever the archwire has a cross-section dimension exceeding a certain, predetermined threshold.

EMBODIMENTS

1. An orthodontic appliance comprising:
    a base having a bonding surface for attachment to a tooth; a body extending outwardly from the base and an elongated slot thereon extending along a generally mesial-distal direction; first and second protrusions disposed on the body with the slot extending therebetween; and a clip slidably engaged to the body and movable between open and closed positions, the first protrusion extending into the clip to retain the clip to the body in an interference fit and the second protrusion extending into the clip in its closed position selectively, wherein the clip comprises at least one deflectable portion aligned along a reference plane extending over the slot and wherein the at least one deflectable portion resiliently bends out of the reference plane to traverse the second protrusion as the clip moves between open and closed positions.

2. The orthodontic appliance of embodiment 1, further comprising a pair of undercut channels on the body, wherein the clip further comprises mesial and distal struts received in the pair of undercut channels.

3. The orthodontic appliance of embodiment 2, wherein the clip further comprises first and second open regions located between the mesial and distal struts, the at least one deflectable portion setting the first and second open regions apart from each other.

4. The orthodontic appliance of embodiment 3, wherein the first and second protrusions occupy different open regions when the clip is closed while the first protrusion occupies the second open region and the second protrusion occupies neither open region when the clip is open.

5. An orthodontic appliance comprising:
    a base having a bonding surface for attachment to a tooth;
    a body extending outwardly from the base and having an elongated slot thereon extending along a generally mesial-distal direction;
    a resilient clip comprising mesial and distal struts slidably engaged to the body to enable movement of the clip between open and closed positions, and an open region located between the mesial and distal struts; and
    first and second protrusions disposed on the body with the slot extending therebetween, wherein both protrusions occupy the open region when the clip is closed and only the first protrusion occupies the open region when the clip is open.

6. The orthodontic appliance of embodiment 5, wherein the open region comprises a first open region and further comprising a second open region adjacent the first open region, and at least one deflectable portion setting the first and second open regions apart from each other.

7. The orthodontic appliance of embodiment 6, wherein the at least one deflectable portion is aligned along a reference plane extending over the slot, the deflectable portion resiliently bending out of the reference plane to traverse the first protrusion as the clip slides between open and closed positions.

8. The orthodontic appliance of any of embodiments 4 to 7, wherein the at least one deflectable portion comprises a pair of tabs protruding inwardly from the mesial and distal struts toward each other.

9. The orthodontic appliance of embodiment 8, wherein the open regions have a certain mesial-distal width and the pair of tabs are spaced apart by a gap that ranges from 5 percent to 80 percent of the certain mesial-distal width.

10. The orthodontic appliance of embodiment 9, wherein the gap ranges from 15 percent to 60 percent of the certain mesial-distal width.

11. The orthodontic appliance of embodiment 10, wherein the gap ranges from 45 percent to 60 percent of the certain mesial-distal width.

12. The orthodontic appliance of embodiment 9, wherein the second protrusion has an overall mesial-distal width greater than the certain mesial-distal width.

13. The orthodontic appliance of embodiment 12, wherein the second protrusion comprises two or more subprotrusions that collectively have the overall mesial-distal width.

14. The orthodontic appliance of embodiment any of the previous embodiments, wherein the first protrusion generally extends in a direction away from the base while the second protrusion generally extends in a direction toward the base.

15. The orthodontic appliance of any of the previous embodiments, wherein both the first and second protrusions generally extend in a direction toward the base.

16. The orthodontic appliance of any of embodiments 3, and 7-15, wherein the second open region is collectively defined by the mesial and distal struts and at least one deflectable portion, the at least one deflectable portion comprising a front strut mutually connecting the mesial and distal struts, wherein the front strut resiliently bends to traverse the second protrusion as the clip slides between open and closed positions.

17. The orthodontic appliance of embodiment 16, wherein the clip further comprises a back strut mutually connecting the mesial and distal struts, wherein the back strut, the mesial and distal struts, and at least one deflectable portion collectively define the first open region.

18. The orthodontic appliance of embodiment 17, wherein the first and second protrusions simultaneously engage the front and back struts, respectively, while the clip is in its closed position to restrict sliding movement of the clip.

19. The orthodontic appliance of embodiment 17, wherein the first protrusion simultaneously engages the front strut and the at least one deflectable portion when the clip is in its open position to restrict sliding movement of the clip.

20. The orthodontic appliance of embodiment 16, wherein the body comprises an angled wall adjacent the second protrusion, wherein the angled wall contacts the front strut and urges the clip toward the base when the clip is closed.

21. The orthodontic appliance of embodiments 4 and 6-20, wherein the at least one deflectable portion comprises an intermediate strut interconnecting the mesial and distal struts.

22. The orthodontic appliance of any of the previous embodiments, wherein the overall clip is generally aligned along the reference plane.

23. The orthodontic appliance of any of the previous embodiments, wherein the slot has a pair of opposing side walls and a bottom wall perpendicular to the side walls, the reference plane being generally parallel the bottom wall.

24. A method of using an orthodontic appliance comprising:
    providing the appliance comprising a base, a body extending outwardly from the base, an elongated slot extending along a generally mesial-distal direction disposed on the base, and first and second protrusions located on the body on opposite sides of the slot; providing a clip having an open region slidably engaged to the body, wherein the first protrusion occupies the open region to retain the clip in an interference fit and the second protrusion resides outside of the open region; sliding the clip from an open position toward a closed position whereby a first deflectable portion of the clip urges against the second protrusion; and resiliently bending the first deflectable portion to enable the clip to traverse the second protrusion and position both the first and second protrusions within the open region to retain the clip in the closed position.

25. The method of embodiment 24, wherein the open region comprises a first open region and a second open region adjacent the first open region, and further comprising a second deflectable portion setting the first and second open regions apart from each other.

26. The method of embodiment 25, wherein the second deflectable portion is aligned along a reference plane extending over the slot, and further comprising resiliently bending the second deflectable portion out of the reference plane to traverse the first protrusion as the clip slides toward its closed position.

27. The method of embodiment 26, wherein the clip further comprises mesial and distal struts and the second deflectable portion comprises a pair of tabs protruding inwardly from the mesial and distal struts.

All of the patents and patent applications mentioned above are hereby expressly incorporated into the present description. The foregoing invention has been described in some detail by way of illustration and example for purposes of clarity and understanding. However, various alternatives, modifications, and equivalents may be used and the above description should not be taken as limiting in the scope of the invention which is defined by the following claims and their equivalents.

What is claimed is:

1. An orthodontic appliance comprising:
a base having a bonding surface for attachment to a tooth;
a body extending outwardly from the base and an elongated slot thereon extending along a generally mesial-distal direction, the body further comprising a pair of undercut channels on the body;
first and second protrusions disposed on the body with the slot extending therebetween, the second protrusion extending in a direction towards the base; and
a clip comprising mesial and distal struts each received in one of the pair of undercut channels, slidably engaged to the body and movable between open and closed positions, the first protrusion extending into the clip to retain the clip to the body in an interference fit and the second protrusion extending into the clip in its closed position selectively, wherein the clip comprises at least one deflectable portion aligned along a reference plane extending over the slot and wherein the at least one deflectable portion resiliently bends out of the reference plane in a direction towards the base to traverse the second protrusion as the clip moves between open and closed positions,
wherein the clip further comprises first and second open regions located between the mesial and distal struts, the at least one deflectable portion setting the first and second open regions apart from each other.

2. The orthodontic appliance of claim 1, wherein the first and second protrusions occupy different open regions when the clip is closed while the first protrusion occupies the second open region and the second protrusion occupies neither open region when the clip is open.

3. An orthodontic appliance comprising:
a base having a bonding surface for attachment to a tooth;
a body extending outwardly from the base and having an elongated slot thereon extending along a generally mesial-distal direction, the body including a channel on at least one side of the slot,
a resilient clip comprising mesial and distal struts slidably engaged to the body to enable movement of the clip between open and closed positions, and an open region located between the mesial and distal struts; and
first and second protrusions disposed on the body with the slot extending therebetween, wherein the second protrusion generally extends in a direction toward the base into the channel, wherein both protrusions occupy the open region when the clip is closed and only the first protrusion occupies the open region when the clip is open.

4. The orthodontic appliance of claim 3, wherein the open region comprises a first open region and further comprising a second open region adjacent the first open region, and at least one deflectable portion setting the first and second open regions apart from each other.

5. The orthodontic appliance of claim 4, wherein the at least one deflectable portion is aligned along a reference plane extending over the slot, the deflectable portion resiliently bending out of the reference plane to traverse the first protrusion as the clip slides between open and closed positions.

6. The orthodontic appliance of claim 2, wherein the at least one deflectable portion comprises a pair of tabs protruding inwardly from the mesial and distal struts toward each other.

7. The orthodontic appliance of claim 6, wherein the open regions have a certain mesial-distal width between the mesial and distal struts, and the pair of tabs are spaced apart by a gap that ranges from 5 percent to 80 percent of the certain mesial-distal width.

8. The orthodontic appliance of claim 7, wherein the gap ranges from 15 percent to 60 percent of the certain mesial-distal width.

9. The orthodontic appliance of claim 7, wherein the second protrusion has an overall mesial-distal width greater than the certain mesial-distal width.

10. The orthodontic appliance of claim 9, wherein the second protrusion comprises two or more subprotrusions that collectively define the overall mesial-distal width.

11. The orthodontic appliance of claim 1, wherein the first protrusion generally extends in a direction away from the base while the second protrusion generally extends in a direction toward the base.

12. The orthodontic appliance of claim 1, wherein both the first and second protrusions generally extend in a direction toward the base.

13. The orthodontic applicant of claim 1, wherein the second open region is collectively defined by the mesial and distal struts and at least one deflectable portion, the at least one deflectable portion comprising a front strut mutually connecting the mesial and distal struts, wherein the front strut resiliently bends to traverse the second protrusion as the clip slides between open and closed positions.

14. The orthodontic appliance of claim 13, wherein the clip further comprises a back strut mutually connecting the mesial and distal struts, wherein the back strut, the mesial and distal struts, and at least one deflectable portion collectively define the first open region.

15. The orthodontic appliance of claim 14, wherein the body comprises an angled wall adjacent the second protrusion, wherein the angled wall contacts the front strut and urges the clip toward the base when the clip is closed.

16. The orthodontic appliance of claim 4, wherein the at least one deflectable portion comprises an intermediate strut interconnecting the mesial and distal struts.

17. The orthodontic appliance of claim 1, wherein the overall clip is generally aligned along the reference plane.

18. The orthodontic appliance of claim 1, wherein the slot has a pair of opposing side walls and a bottom wall perpendicular to the side walls, the reference plane being generally parallel to the bottom wall.

19. A method of using an orthodontic appliance comprising:
providing the appliance comprising a base, a body extending outwardly from the base, an elongated slot extending along a generally mesial-distal direction disposed on the base, and first and second protrusions located on the body on opposite sides of the slot;
providing a clip having an open region slidably engaged to the body, wherein the first protrusion occupies the open region to retain the clip in an interference fit and the second protrusion resides outside of the open region;
sliding the clip from an open position toward a closed position whereby a first deflectable portion of the clip urges against the second protrusion; and
resiliently bending the first deflectable portion in a direction towards the base to enable the clip to traverse the second protrusion and position both the first and second protrusions within the open region to retain the clip in the closed position.

\* \* \* \* \*